United States Patent
Rodriguez et al.

(10) Patent No.: US 9,187,389 B2
(45) Date of Patent: Nov. 17, 2015

(54) METHOD TO PRODUCE ALCOHOLS FROM ORGANIC ACIDS

(71) Applicants: Brandon A. Rodriguez, Freeport, TX (US); Jose A. Trejo O'Reilly, Lansdale, PA (US)

(72) Inventors: Brandon A. Rodriguez, Freeport, TX (US); Jose A. Trejo O'Reilly, Lansdale, PA (US)

(73) Assignees: Rohm and Haas Company, Philadelphia, PA (US); Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/417,576

(22) PCT Filed: Aug. 13, 2013

(86) PCT No.: PCT/US2013/054606
§ 371 (c)(1),
(2) Date: Jan. 27, 2015

(87) PCT Pub. No.: WO2014/035654
PCT Pub. Date: Mar. 6, 2014

(65) Prior Publication Data
US 2015/0251982 A1     Sep. 10, 2015

Related U.S. Application Data

(60) Provisional application No. 61/695,557, filed on Aug. 31, 2012.

(51) Int. Cl.
C07C 27/04 (2006.01)
C07C 27/00 (2006.01)
C07C 29/149 (2006.01)

(52) U.S. Cl.
CPC ................... *C07C 29/149* (2013.01)

(58) Field of Classification Search
CPC ...... C07C 29/149; C07C 31/08; C07C 31/10; C07C 31/25
USPC .................................. 568/876, 884
See application file for complete search history.

(56) References Cited

U.S. PATENT DOCUMENTS

| | | | |
|---|---|---|---|
| 2,366,007 | A | 12/1944 | D'Alelio |
| 2,500,149 | A | 3/1950 | Boyer |
| 3,037,052 | A | 5/1962 | Bortnick |
| 5,030,609 | A | 7/1991 | Turner et al. |
| 5,248,435 | A | 9/1993 | Morita et al. |
| 6,228,896 | B1 | 5/2001 | Bachmann et al. |
| 6,750,259 | B2 | 6/2004 | Dimotsis et al. |
| 6,784,213 | B2 | 8/2004 | Rohrbach et al. |
| 7,935,834 | B2 | 5/2011 | Bhattacharyya et al. |
| 2002/0002267 | A1 | 1/2002 | Long |
| 2004/0006145 | A1 | 1/2004 | Dimotsis et al. |
| 2010/0029995 | A1 | 2/2010 | Johnston et al. |

FOREIGN PATENT DOCUMENTS

| | | |
|---|---|---|
| EP | 301853 | 2/1992 |
| GB | 2150560 | 7/1985 |
| WO | 8203854 | 11/1982 |

OTHER PUBLICATIONS

Calore, et al. Reactive and Functional Polymers 70 (2010) 639-646.
Dow catalyst brochure: AMBERLIST Polymeric Catalysts.

*Primary Examiner* — Jafar Parsa
(74) *Attorney, Agent, or Firm* — Edward W. Black

(57) ABSTRACT

A method of producing an alcohol compound from an organic acid compound including the step of heating a solution of the organic acid compound in the presence of a heterogeneous catalyst including transition metal supported upon a cross-linked functional polymer.

8 Claims, No Drawings

METHOD TO PRODUCE ALCOHOLS FROM ORGANIC ACIDS

FIELD

The invention relates to producing alcohols from organic acids using a single catalyst.

INTRODUCTION

Conventional methods for producing alcohols from acids involve multi-step processes including at least two distinct catalysts. For example, the conversion of an organic acid to a corresponding ester is commonly catalyzed by a strong acid polymer catalyst (e.g. AMBERLYST 70, AMBERLYST 15Wet) at a relatively low temperature (e.g. less than 100° C., see for example U.S. Pat. No. 3,037,052) followed by subsequent conversion to an alcohol at a relatively high temperature (e.g. over 240° C.), catalyzed by a copper-chromite catalyst (see for example U.S. Pat. No. 5,030,609). The use of multiple catalysts, high temperatures and chromium-containing compounds results in an expensive and complex process.

SUMMARY

The invention includes a method that at least partially addresses the shortcomings noted above. In one embodiment, the invention includes a method of producing an alcohol compound from an organic acid compound comprising the step of heating a solution of the organic acid compound in the presence of a heterogeneous catalyst comprising a transition metal supported upon a cross-linked functional polymer. In a preferred embodiment, the method is conducted in a single vessel without the presence of chromium or other catalysts. Many additional embodiments are described.

DETAILED DESCRIPTION

The invention includes a method for producing an alcohol compound from an organic acid compound. In a preferred embodiment, the method is conducted using a single catalyst capable of catalyzing both esterfication and reduction reactions. The method may be conducted in a single vessel as part of a batch or continuous process. For example, an alcohol compound, organic acid compound, hydrogen, and the subject catalyst may be combined in a common vessel. The catalyst (principally the strong acid support) catalyzes a Fischer esterfication reaction of the alcohol and acid. The resulting ester containing-compound is subsequently reduced to form the desired mono or di-alcohol compound. Both the esterfication and reduction reactions are catalyzed by the same catalyst. In a preferred embodiment, no other catalysts, particularly chromium containing species such as copper chromite, are used.

The method includes the step of heating a solution of an organic acid compound and an alcohol compound in the presence of a heterogeneous catalyst comprising a known hydrogenation metals supported upon a cross-linked functional polymer to a temperature less than 200° C., and more preferably less than 190° C., (e.g. from 70 to 200° C., more preferably from 80 to 190° C., and still more preferably from 90 to 185° C.). During heating the solution is preferably maintained a pressure of less than 70 bar, more preferably less than 60 bar, (e.g. from 40 to 70 bar and more preferably from 45 to 60 bar).

The selection of solvent for use in the solution is not particularly limited so long as the aforementioned alcohol and organic acid compounds are soluble. Non-limiting examples include: water, ethanol, propanol, propyl ester, methyl isobutyl ketone and tetrahydrofuran. The use of an alcohol solvent can be used to correspond to the resultant product so as to yield a simple chemical reaction profile. Additionally, the solvent used can be tuned to be less miscible with the product so as to yield desirable separations processes.

The invention is applicable to a broad range of organic acid compounds, i.e. organic acid compounds including at least one carboxylic acid functional group. One preferred class includes compounds having molecular weights of less than 300 Daltons, preferably less than 200 Daltons and in some embodiments less than 150 Daltons. One preferred subclass of compounds includes two carboxylic acid functional groups, i.e. "dicarboxylic acids." In another embodiment, a preferred class of organic acid compounds includes saturated and unsaturated compounds represented by the formula:

R—COOH wherein R is a hydrocarbon moiety selected from substituted (e.g. with a carboxylic acid group) or unsubstituted aliphatic and aromatic groups. In a preferred subclass of embodiments, the hydrocarbon moiety comprises from 2 to 12, and some embodiments from 2 to 8 carbon atoms. Representative examples of compounds where R is an aliphatic moiety include: formic, acetic, propionic, prop-2-enoic, butyric, valeric, caproic, ethanthic, caprylic, pelaronic capric, undecyclic, lauric, tridecylic and myristic acid. Representative examples of applicable dicarboxylic acids where R is an aliphatic moiety include: oxalic, malonic, succinic acid, glutaric, adipic, pimelic, suberic, azelaic and sebacic acid. Representative examples of where R is an aromatic moiety include: benzoic, isophthalic and terephthalic acid, naphthalic and cinnamic acid.

The scope of applicable heterogeneous catalysts is not particularly limited so long as they include a transition metal (e.g. Cu, Ru, Pt, Rh), preferably copper, supported upon a cross-linked functional polymer. In a preferred embodiment, the support also serves as a catalyst, particularly during the conversion of the organic acid compound to a corresponding ester. In one embodiment, the cross-linked functional polymer is a cross-linked copolymer matrix including sulfonic acid functional groups, such as a strong acid cationic exchange resin. In a preferred sub-embodiment, the cross-linked copolymer matrix comprises a reaction product of a monomer mixture comprising styrene and divinylbenzene. The matrix may have a macro reticular, gellular, or interpenetrating polymer network structure and is preferably provided in a bead form, which may have a uniform size distribution or Gaussian distribution, (as those terms are commonly understood in the ion exchange art). The matrix may be subsequently sulfonated by combining copolymer matrix with a sulfonating agent such as sulfuric acid, chlorosulfonic acid or sulfur trioxide, with or without a swelling agent. The reaction is preferably conducted at elevated temperature, e.g. 100-150° C. See for example: U.S. Pat. Nos. 2,366,007, 2,500,149, 3,037,052, 5,248,435, 6,228,896, 6,750,259, 6,784,213, US 2002/002267 and US 2004/0006145. Commercially available cross-linked functional polymers include DOWEX 50WX8 or AMBERLYST 35, both strong acid, and gel and macro reticular resin respectively available from The Dow Chemical Company. The a cross-linked functional polymer may be impregnated with hydrogenation metal ion by soaking the polymer in a solution containing hydrogenation metal salt at room temperature followed by rinsing and drying; see for example, Calore, et al., Metal Catalyst with Nano-structured Metals Supported on Strongly Acidic Cross-linked Polymer Frameworks. Part I., Reactive & Functional Polymers 70 (2010) 639-646. The hydrogenation metal ion can be reduced to metal, zero valence, before use or preferably reduced during use by hydrogen reduction. A preferred hydrogenation metal salt is copper sulfate. In a preferred embodiment, the catalyst contains no chromium species.

Other examples of suitable cross-linked functional polymers include silica/nafion micro-composite materials such as Dupont's SAC-13, which may be loaded with copper according to the method described in Calore, et al.

EXAMPLES

The experiments described below were conducted using solutions consisting of 125 ml of an acid and alcohol (1:4 volume ratio) designated below along with hydrogen and catalyst, charged in a 450 mL Parr reactor. All catalysts are designated by their trade names in the Tables below and were obtained from The Dow Chemical Company. Reactions were conducted at a run temperature of 180° C. and pressure of 55.2 bar (800 psi) for approximately 3 hours. Final percentages and volumes (mL) of acid, ester and alcohol products of each reaction are specified in the Tables below. The following abbreviations are used in the Tables and are defined as follows:

EA ethyl acetate
PP propyl propionate
OO octanoate
AA acrylic acid
PA propionic acid
OA octanoic acid
EOH ethanol
POH propanol
OOH octanol
MO methyl octanoate Comparative Example 1

Aqueous solutions where prepared included propionic acid and propanol in a 1:4 volume ratio with 4 grams of the catalyst designated below in Table 1. The catalysts were not impregnated with metal. Note the low conversion of propionic acid (PA) to propanol (POH), i.e. ratios of PA:POH of no greater than 1:5.1.

TABLE 1

| Catalyst | % PP | % PA | % POH | PA:POH (final) | PA (final) | POH (final) | PP (final) |
|---|---|---|---|---|---|---|---|
| A-15 | 32.2 | 21.1 | 46.7 | 1:2.2 | 26.375 | 58.375 | 40.25 |
| A-16 | 33.7 | 18.3 | 48 | 1:2.7 | 22.875 | 60 | 42.125 |
| A-35 | 34.4 | 16.7 | 48.8 | 1:3.0 | 20.875 | 61 | 43.125 |
| A-70 | 34.4 | 15.1 | 50.6 | 1:3.4 | 18.875 | 63.25 | 42.875 |
| A-121 | 34.7 | 10.6 | 54.6 | 1:5.1 | 13.25 | 68.25 | 43.5 |
| 50 W × 8 | 34.1 | 15.6 | 51 | 1:3.3 | 19.5 | 63.75 | 41.75 |

Examples 1-4

In all samples, AMBERLYST A-35 was impregnation by soaking the polymer in a metal salt solution at room temperature for approximately 8-10 hours. Final metal content is expressed as a weight percent of the total catalyst weight. The total amount of catalyst added to each reaction solution is specified in the Tables.

TABLE 2

| Catalyst | % EA | % AA | % EOH | AA:EOH (final) | AA (final) | EOH (final) | EA (final) |
|---|---|---|---|---|---|---|---|
| 2 wt % Cu (1 g catalyst) | 22.7 | 4.4 | 72.5 | 1:16.0 | 5.5 | 90.6 | 28.9 |
| 1 wt % Ru (2 g catalyst) | 28.3 | 10.1 | 61.1 | 1:6.0 | 12.6 | 76.4 | 36.0 |
| 1 wt % Pt (2 g catalyst) | 27.3 | 25.5 | 50.9 | 1:2.0 | 31.9 | 63.6 | 29.5 |

TABLE 3

| Catalyst | % PP | % PA | % POH | PA:POH (final) | PA (final) | POH (final) | PP (final) |
|---|---|---|---|---|---|---|---|
| 22 wt % Rh (4 g catalyst) | 38.8 | 16.4 | 44.6 | 1:2.7 | 20.5 | 55.75 | 48.75 |
| 2 wt % Pt (4 g catalyst) | 36.9 | 24 | 38.8 | 1:1.7 | 30 | 48.5 | 46.5 |
| 2 wt % Cu (4 g catalyst) | 33.4 | 3 | 63.1 | 1:20.0 | 3.75 | 78.875 | 42.375 |
| 1 wt % Ru (2 g catalyst) | 37.1 | 11.6 | 51.2 | 1:2.5 | 14.5 | 64 | 46.5 |
| 1 wt % Pt (2 g catalyst) | 35.1 | 18.2 | 46.4 | 1:2.5 | 22.75 | 58 | 44.25 |
| 1 wt % Ru/Pt (1:1 wt ratio) (2 g catalyst) | 36.7 | 15.8 | 47.4 | 1:3.0 | 19.75 | 59.25 | 46 |
| 2 wt % Cu (1 g catalyst) | 33.3 | 4.3 | 62.2 | 1:14.0 | 5.375 | 77.75 | 41.875 |

TABLE 4

| Catalyst | % OO | % OA | % OOH | OA:OOH (final) | OA (final) | OOH (final) | OO (final) |
|---|---|---|---|---|---|---|---|
| 2 wt % Cu (1 g catalyst) | 18.3 | 8.7 | 73 | 1:8.4 | 10.875 | 91.25 | 22.875 |
| 1 wt % Ru (2 g catalyst) | 22.2 | 6.4 | 71.4 | 1:11.5 | 8 | 89.25 | 27.75 |
| 1 wt % Pt (2 g catalyst) | 24.5 | 4.2 | 71.2 | 1:16.9 | 5.25 | 89 | 30.75 |

TABLE 5

| Catalyst | % MO | % OA | % OOH | OA:OH (final) | OA (final) | OOH (final) | MO (final) |
|---|---|---|---|---|---|---|---|
| A-35 2% Cu (1 g catalyst) | 33.83* | 0 | 30.6* | 0 | | 38.3* | 42.3* |

*Contains a mixture of octanol and methanol. Number above corresponds to octanol only.

Many embodiments of the invention have been described and in some instances certain embodiments, selections, ranges, constituents, or other features have been characterized as being "preferred." Characterizations of "preferred" features should in no way be interpreted as deeming such features as being required, essential or critical to the invention.

The invention claimed is:

1. A method of producing an alcohol compound from an organic acid compound comprising the step of heating a solution of the organic acid compound in the presence of hydrogen and a heterogeneous catalyst comprising a transition metal selected from at least one of: Cu, Ru, Pt and Rh supported upon a cross-linked functional polymer comprising a cross-liked copolymer matrix including sulfonic acid functional groups.

2. The method of claim 1 wherein the cross-linked copolymer matrix comprises a reaction product of a monomer mixture comprising styrene and divinylbenzene.

3. The method of claim 1 wherein the cross-linked functional polymer comprises a strong acid cationic exchange resin.

4. The method of claim 1 wherein the method is conducted without the presence of chromium.

5. The method of claim 1 conducted in the presence of the heterogeneous catalyst as the sole catalyst.

6. The method of claim 1 wherein the step of heating comprises heating the solution to a temperature less than 200° C.

7. The method of claim 1 wherein the step of heating comprises heating the solution to a temperature less than 190° C. and a pressure of less than 70 bar.

8. The method of claim 1 wherein the method is conducted in a single vessel.

* * * * *